US009946845B2

(12) United States Patent
Holmes

(10) Patent No.: US 9,946,845 B2
(45) Date of Patent: Apr. 17, 2018

(54) SYSTEM AND METHOD FOR FILLING AND DISPENSING ORDERS

(71) Applicant: RxSafe, LLC, San Marcos, CA (US)

(72) Inventor: William K. Holmes, San Diego, CA (US)

(73) Assignee: RXSAFE LLC, Vista, CA (US)

( * ) Notice: Subject to any disclaimer, the term of this patent is extended or adjusted under 35 U.S.C. 154(b) by 484 days.

(21) Appl. No.: 13/963,837

(22) Filed: Aug. 9, 2013

(65) Prior Publication Data
US 2014/0094960 A1 Apr. 3, 2014

Related U.S. Application Data

(63) Continuation-in-part of application No. 13/804,818, filed on Mar. 14, 2013.

(60) Provisional application No. 61/708,935, filed on Oct. 2, 2012.

(51) Int. Cl.
G06F 7/00 (2006.01)
G06F 19/00 (2018.01)
G07F 17/00 (2006.01)

(52) U.S. Cl.
CPC ...... G06F 19/3462 (2013.01); G07F 17/0092 (2013.01)

(58) Field of Classification Search
CPC .......................... G06F 19/3462; G07F 17/0092
USPC .......................................................... 700/216
See application file for complete search history.

(56) References Cited

U.S. PATENT DOCUMENTS

| 4,267,942 | A | * | 5/1981 | Wick, Jr. ............ G07C 9/00896 194/213 |
| 5,901,876 | A | * | 5/1999 | Yuyama ................ A61J 7/0084 221/124 |
| 5,905,653 | A | | 5/1999 | Higham et al. |
| 6,048,086 | A | | 4/2000 | Valerino, Sr. |
| 6,711,460 | B1 | | 3/2004 | Reese |
| 6,883,681 | B1 | * | 4/2005 | Coughlin .............. G07F 11/165 221/123 |
| 7,672,859 | B1 | | 3/2010 | Louie |
| 2001/0027634 | A1 | | 10/2001 | Hebron et al. |
| 2004/0004085 | A1 | | 1/2004 | Williams |
| 2004/0034447 | A1 | | 2/2004 | Vollm |
| 2004/0059463 | A1 | * | 3/2004 | Coughlin .............. G07F 11/165 700/229 |

(Continued)

OTHER PUBLICATIONS

International Search Report and Written Opinion for Application No. PCT/US2013/62866 dated Jun. 5, 2014 (22 pages).

(Continued)

Primary Examiner — Kyle O Logan
(74) Attorney, Agent, or Firm — Michael Best & Friedrich LLP

(57) ABSTRACT

A method of filling prescription orders includes inputting the prescription orders into a pharmaceutical storage and retrieval device, processing the prescription orders with the pharmaceutical storage and retrieval device to fill a plurality of vials with desired pharmaceuticals, and transferring the plurality of filled vials from the pharmaceutical storage and retrieval device to a storage unit. The method also includes storing the plurality of filled vials in the storage unit until a customer claims one of the plurality of filled vials and directing the one of the plurality of filled vials from the storage unit to the customer.

20 Claims, 13 Drawing Sheets

(56) References Cited

U.S. PATENT DOCUMENTS

| | | |
|---|---|---|
| 2004/0093116 A1 | 5/2004 | Mountz |
| 2005/0192705 A1 | 9/2005 | Pinney et al. |
| 2006/0106488 A1 | 5/2006 | Zito, Jr. |
| 2006/0161296 A1 | 7/2006 | Shoenfeld |
| 2006/0277269 A1 | 12/2006 | Dent et al. |
| 2007/0043469 A1 | 2/2007 | Draper |
| 2008/0247858 A1* | 10/2008 | Lourman ............ B41F 15/0872 414/779 |
| 2010/0030667 A1 | 2/2010 | Chudy et al. |
| 2010/0228392 A1* | 9/2010 | Braun ................ A61G 12/001 700/242 |
| 2011/0046778 A1 | 2/2011 | Pinney et al. |
| 2011/0054668 A1* | 3/2011 | Holmes ............ G06Q 20/40145 700/216 |
| 2011/0125314 A1* | 5/2011 | Robinson ................ C12Q 1/04 700/228 |
| 2011/0184751 A1* | 7/2011 | Holmes ............... G06F 19/3462 705/2 |
| 2012/0073241 A1* | 3/2012 | Mahar ................ G01G 19/4148 53/55 |
| 2012/0118910 A1* | 5/2012 | Pinney ............... G06F 19/3462 221/133 |

OTHER PUBLICATIONS

United States Patent and Trademark Office Action for U.S. Appl. No. 13/804,818 dated Nov. 30, 2015 (13 pages).
Extended European Search Report from the European Patent Office for Application No. 13844463.3 dated May 30, 2016 (7 pages).

* cited by examiner

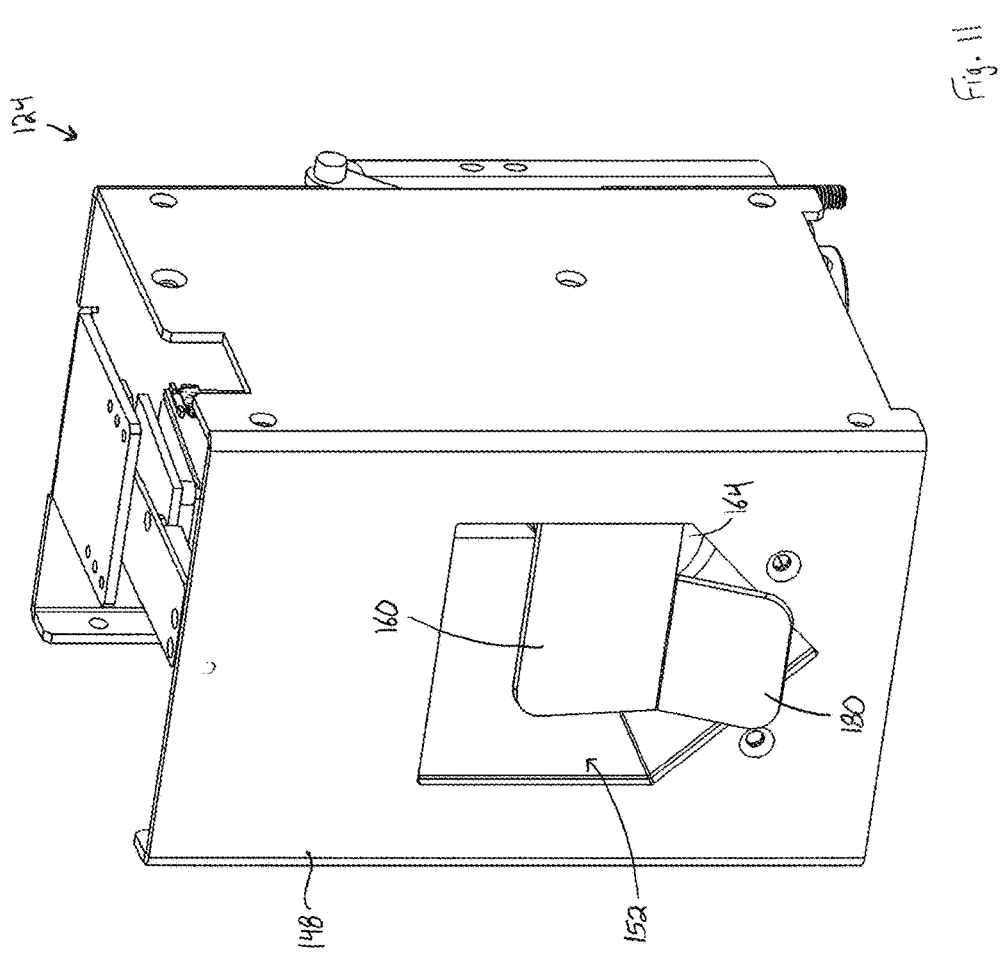

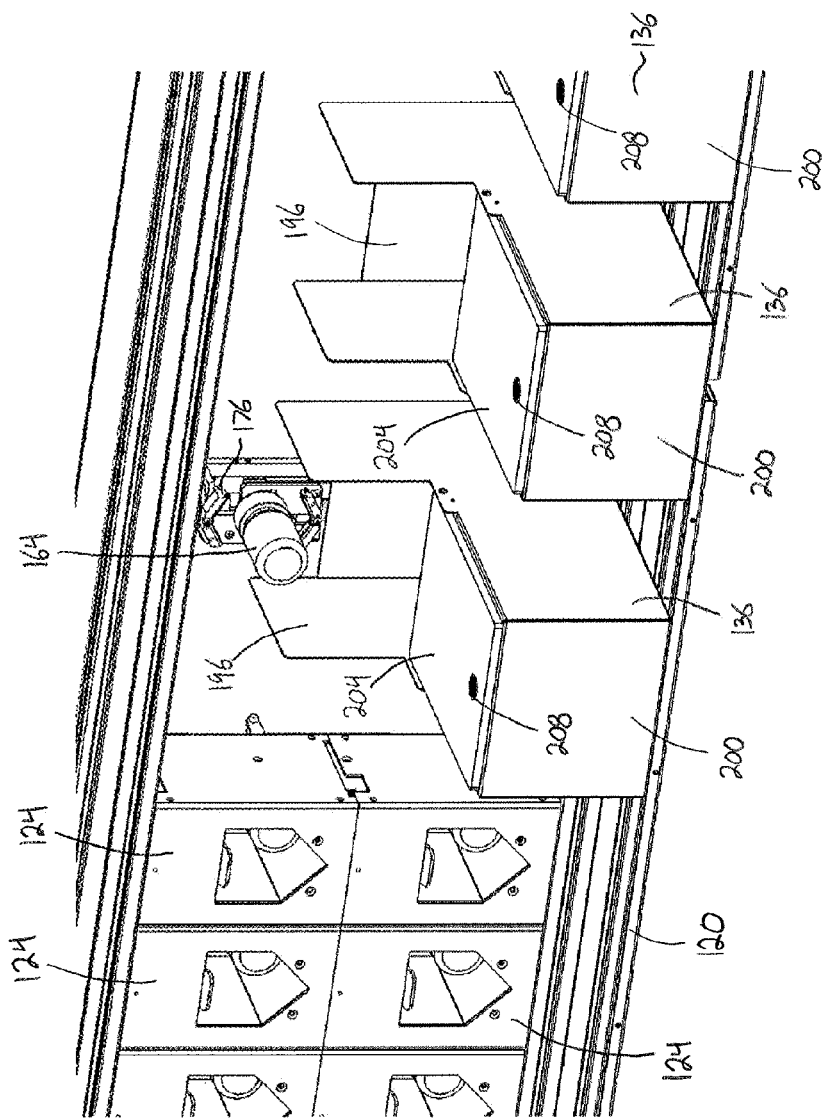

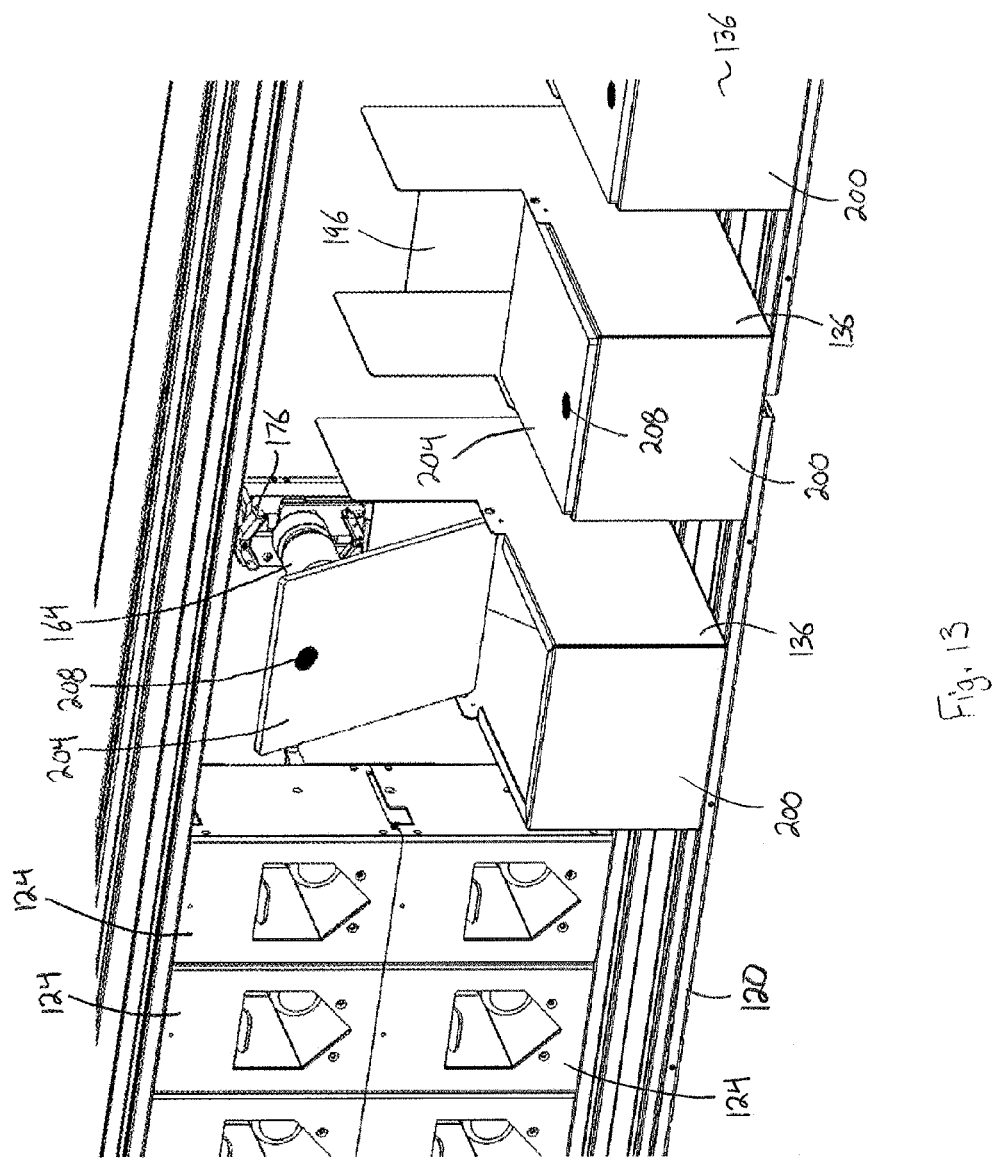

SYSTEM AND METHOD FOR FILLING AND DISPENSING ORDERS

CROSS-REFERENCE TO RELATED APPLICATIONS

This application is a continuation-in-part of U.S. patent application Ser. No. 13/804,818, filed Mar. 14, 2013, and claims priority to U.S. Provisional Patent Application No. 61/708,935, filed Oct. 2, 2012, the entire contents of both of which are incorporated by reference herein.

FIELD OF THE INVENTION

The present invention relates to systems and methods for filling and dispensing orders. More particularly, the present invention relates to systems and methods for filling and dispensing prescription orders to customers in retail pharmacy settings.

SUMMARY

In one embodiment, the invention provides a method of filling prescription orders. The method includes inputting the prescription orders into a pharmaceutical storage and retrieval device, processing the prescription orders with the pharmaceutical storage and retrieval device to fill a plurality of vials with desired pharmaceuticals, and transferring the plurality of filled vials from the pharmaceutical storage and retrieval device to a storage unit. The method also includes storing the plurality of filled vials in the storage unit until a customer claims one of the plurality of filled vials and directing the one of the plurality of filled vials from the storage unit to the customer.

In another embodiment, the invention provides a method of restocking unclaimed prescription orders. The method includes filling a vial with pharmaceuticals using a pharmaceutical storage and retrieval device, transferring the filled vial from the pharmaceutical storage and retrieval device to a storage unit, and storing the filled vial in the storage unit until a customer claims the filled vial. The method also includes monitoring a length of time that the filled vial is stored in the storage unit and returning the filled vial to the pharmaceutical storage and retrieval device if the filled vial is unclaimed by the customer after a predetermined period of time.

In yet another embodiment, the invention provides a storage unit for storing and dispensing filled prescription orders. The storage unit includes a frame and a feeder mounted to the frame. The feeder is configured to receive the filled prescription orders. The storage unit also includes a storage structure positioned within the frame. The storage structure is configured to store the filled prescription orders. The storage unit further includes a dispenser mounted to the frame. The dispenser is configured to dispense the filled prescription orders. The storage unit also includes a collection bin mounted to the frame. The collection bin is configured to receive the filled prescription orders. The storage unit further includes a container-moving assembly positioned within the frame. The container-moving assembly is operable to move a filled prescription order from the feeder to the storage structure when the filled prescription order is positioned within the feeder, move the filled prescription order from the storage structure to the dispenser in response to a first command, and move the filled prescription order from the storage structure to the collection bin in response to a second command.

In still another embodiment, the invention provides a method of storing and dispensing filled prescription orders from a storage unit. The storage unit includes a frame, a feeder mounted to the frame, a storage structure positioned within the frame, a dispenser mounted to the frame, a collection bin mounted to the frame, and a container-moving assembly positioned within the frame. The method includes inserting a filled prescription order into the feeder and moving, by the container-moving assembly, the filled prescription order from the feeder to the storage structure. The method also includes moving, by the container-moving assembly, the filled prescription order from the storage structure to one of the dispenser and the collection bin. The container-moving assembly moves the filled prescription order to the dispenser in response to a first command and moves the filled prescription order to the collection bin in response to a second command.

Other aspects of the invention will become apparent by consideration of the detailed description and accompanying drawings.

BRIEF DESCRIPTION OF THE DRAWINGS

FIG. 11 is a front perspective view of the feeder of the storage unit with the positioning member in the second position.

FIG. 12 is a perspective view of a portion of the storage unit illustrating a collection bin in a closed position.

FIG. 13 is a perspective view of the portion of the storage unit illustrating the collection bin in an open position.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
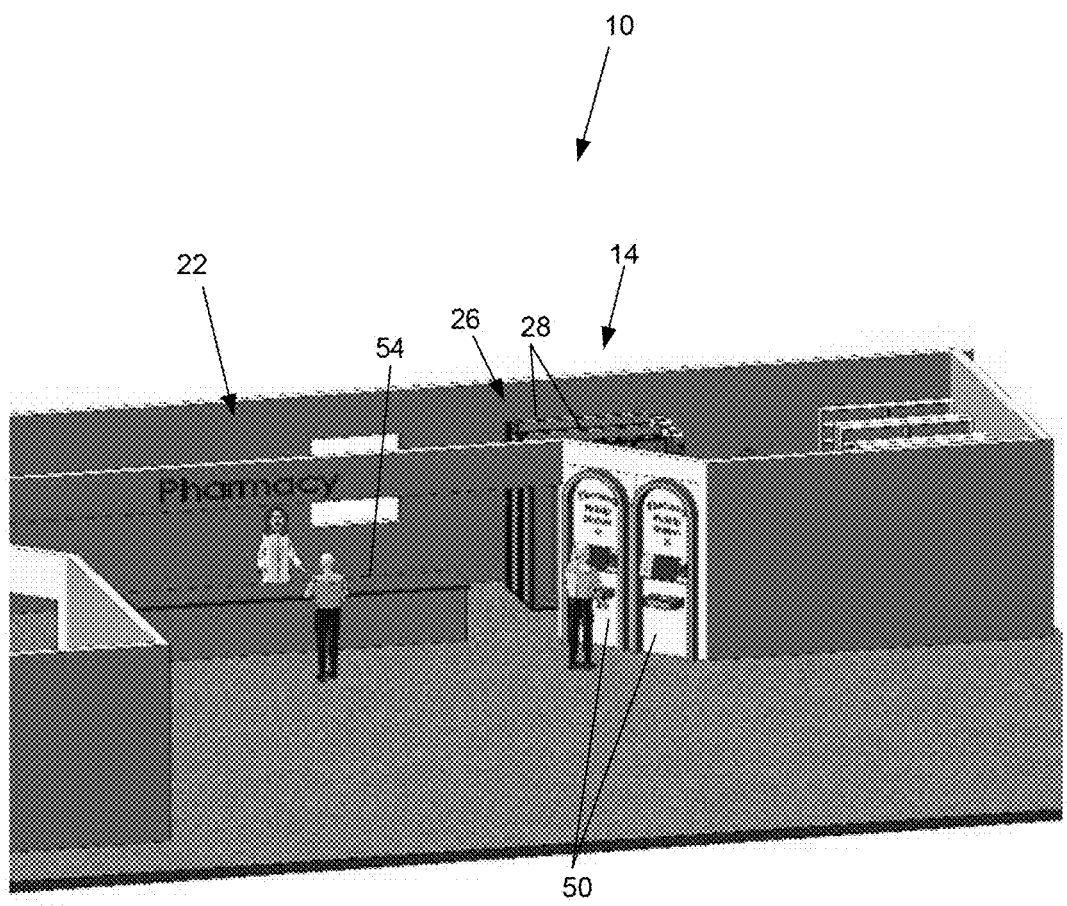
FIG. 1 is a front perspective view of a pharmacy including a system for filling and dispensing orders that embodies the invention.
Figure 2:
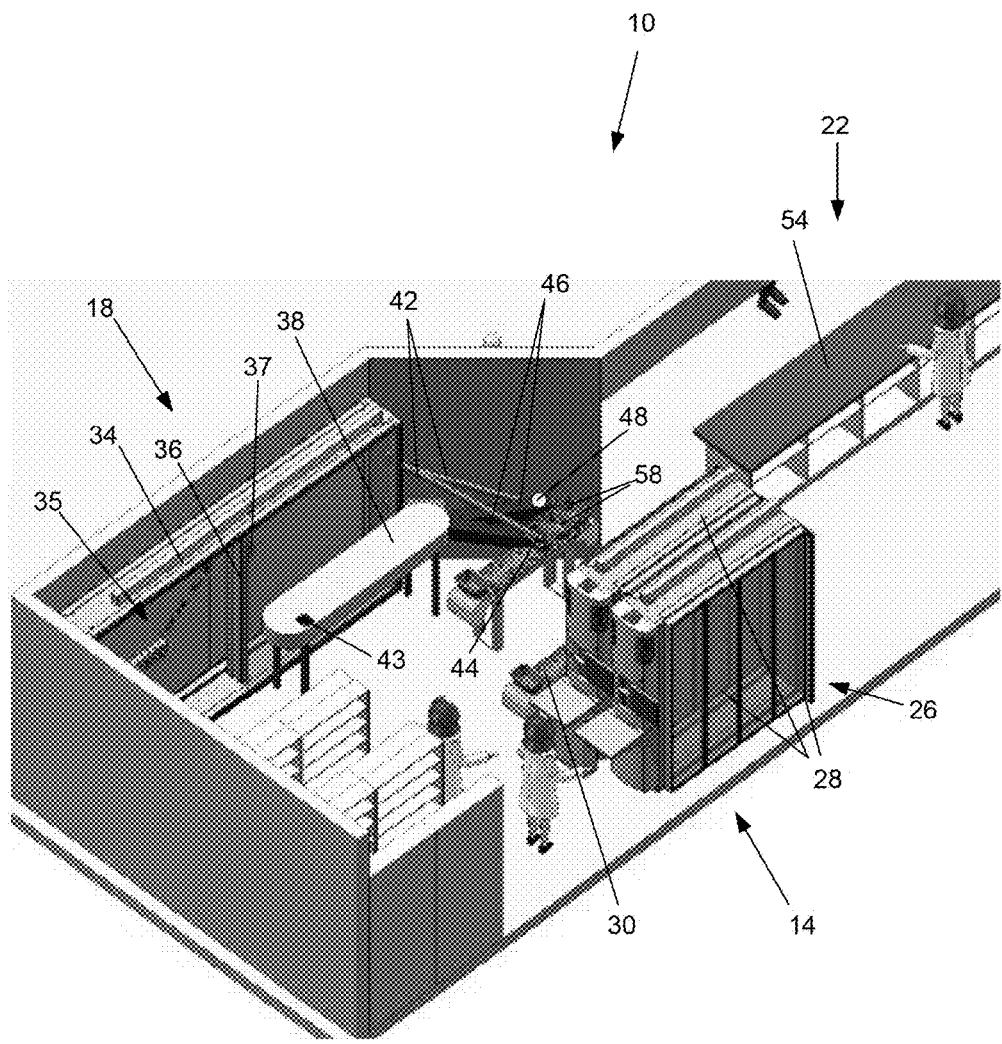
FIG. 2 is a rear perspective view of the pharmacy including the system for filling and dispensing orders.
Figure 3:
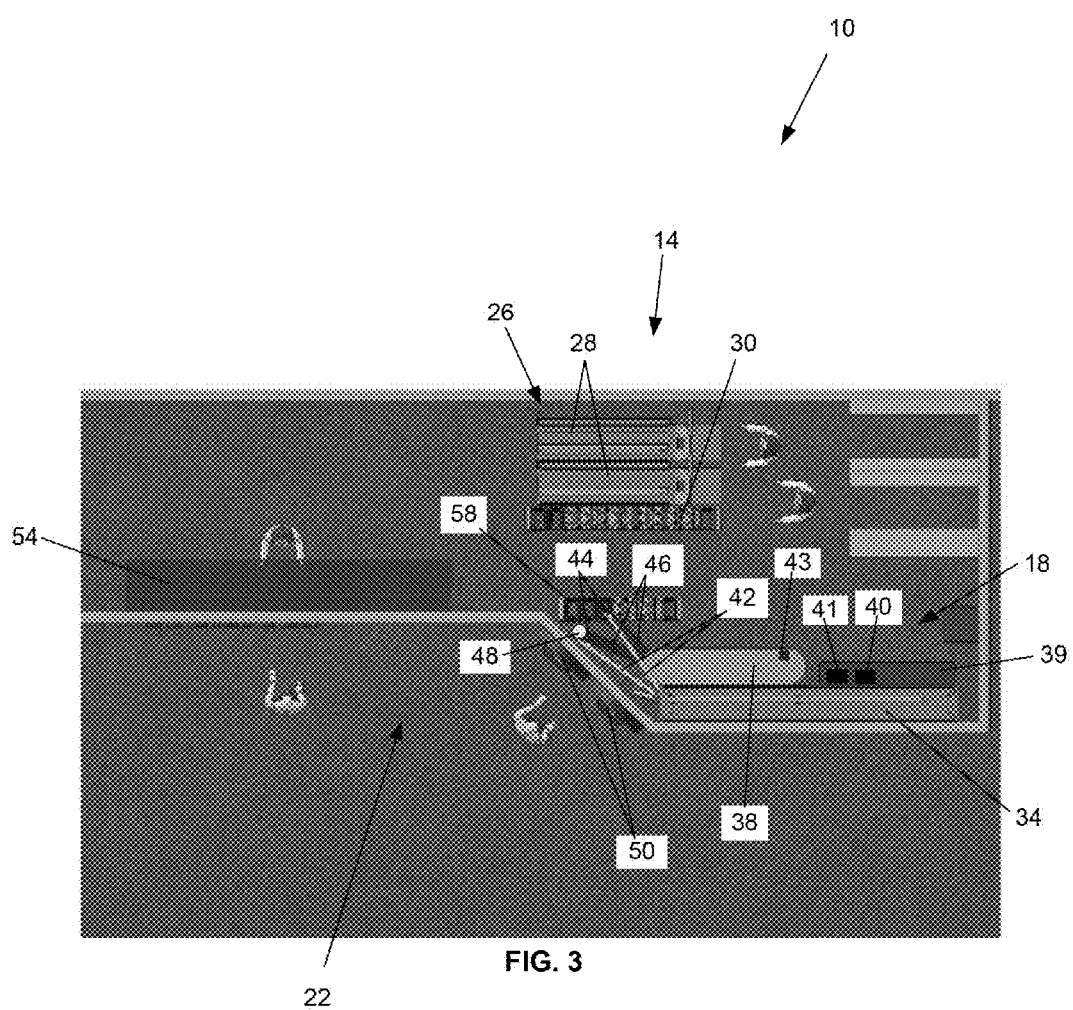
FIG. 3 is a top plan view of the pharmacy including the system for filling and dispensing orders.

FIGS. 1-3 illustrate a system 10 for filling and dispensing prescription drug or other pharmaceutical orders in a pharmacy. The illustrated system 10 includes a production area 14 for filling prescription orders, a will call area 18 for temporarily storing the filled prescriptions, and a sales area 22 for distributing the filled prescriptions to customers. In some embodiments, the filled prescriptions may be patient-specific prescription orders. In other embodiments, the filled prescriptions may be pre-packaged orders of common prescriptions that are assembled before patients request the prescriptions.

The production area 14, or room, is somewhat isolated and out of view of customers to create a more productive factory-like environment for processing and filling orders. The production area 14 may alternatively be visible to customers or managers within the pharmacy. The production area 14 includes a system 26 to fill prescription orders. In the illustrated embodiment, the system 26 includes two pharmaceutical storage and retrieval devices 28. The illustrated devices 28, or towers, are the pharmaceutical storage and retrieval devices disclosed in U.S. patent application Ser. No. 12/870,045, filed Aug. 27, 2010, the entire contents of which are incorporated by reference herein. In other embodiments, the system 26 can include fewer or more pharmaceutical storage and retrieval devices 28, depending on the volume or demand of prescription orders in the pharmacy.

The devices 28 receive and process prescription orders to fill vials and "unit of use" packs with the desired pharmaceuticals (e.g., drugs, narcotics, equipment, etc.). A control system including a processor, memory, and an input device is coupled to the devices 28. The input device allows a user (e.g., a pharmacist or other technician) to input a series of prescription orders into the control system. The devices 28 then process the prescription orders to fill vials or other containers through a partially automated process for particular patients or customers. As discussed in U.S. patent application Ser. No. 12/870,045, each device 28 includes a gantry assembly that moves the pharmaceuticals within the device 28 for access by the user. Operation (e.g., movement) of the gantry assembly is controlled by the control system based on the inputted prescription orders.

After the vials and unit of use packs are filled, the filled vials and packs can be transferred directly to a pharmacist for sale to a customer or can be transferred to the will call area 18 for temporary storage until a customer arrives. For example, filled vials and packs are transferred to the will call area 18 when a customer is coming for next day pickup or at a later time. Conveyors 30 are positioned adjacent the devices 26 to hold the filled vials and packs until the vials and packs can be taken to the will call area 18 or the sales area 22. In some embodiments, the conveyors 30 may be automated and configured to automatically transfer the filled vials and packs to the will call area 18 and/or the sales area 22. The conveyors 30 provide a convenient means to bring the filled vials and packs to the other areas 18, 22 of the pharmacy. In some embodiments, the conveyors 30 may be omitted.

Existing will call systems process prescriptions under the assumption that the prescriptions are sold. That is, the existing systems remove the filled prescriptions from on-hand inventory and decrease a refill counter accordingly, no matter how long the filled prescription sits in will call. However, as much as 20% of filled will call orders are never claimed or are canceled and must be returned to stock. In most states, unclaimed prescriptions typically must be reversed and insurance money must be refunded. Pharmacies, however, normally wait fourteen days before reversing transactions since it is very time consuming to go through and locate unclaimed prescription vials. Furthermore, pharmacies often may believe they are out of a particular drug, yet still have doses of the drug sitting unclaimed in will call which could be utilized to sell a claimed prescription.

In contrast to existing will call systems, the system 10 illustrated in FIGS. 1-3 may place filled prescription vials and packs in a sales pending state. In this state, the total inventory of a particular pharmaceutical (regardless of whether that pharmaceutical is part of a filled prescription) remains visible in the system 10 until a customer actually comes to claim and pick up the filled prescription. Unclaimed pharmaceuticals can thereby be used to fill other prescriptions that are claimed beforehand.

The illustrated will call area 18 includes a storage tower or unit 34 for receiving and storing filled vials from the pharmaceutical storage and retrieval devices 28 in the production area 14. The storage unit 34 receives and stores patient-specific filled vials. That is, the storage unit 34 receives and stores vials including prescription orders that are filled for a particular patient or customer. Additionally or alternatively, the storage unit 34 may receive and store pre-packaged pharmacy vials (e.g., stock vials, non-prescription vials, etc.) that are not patient-specific.

Overall, the storage unit 34 is similar to each of the devices 28, but is a simplified version of one of the devices 28 because the storage unit 34 does not need a user interface. The storage unit 34 is a high-density storage unit that is configured to hold and store over 1000 filled prescription vials at a time. In some embodiments, the storage unit 34 may be about ten feet long and may hold more than 6000 filled vials. In other embodiments, the size of the storage unit 34 may vary to hold fewer or more filled vials, depending on the need of the pharmacy.

As shown in FIG. 2, the storage unit 34 includes a storage space 35 and a gantry assembly 36. The storage space 35 is configured to receive and store the filled vials of pharmaceuticals. Shelves or other suitable structures may be positioned within the storage space 35 to facilitate storing the filled vials in an orderly manner. The gantry assembly 36 is movable within the storage space 35 to position and retrieve the vials. Similar to the gantry assembly disclosed in U.S. patent application Ser. No. 12/870,045, the illustrated gantry assembly 36 includes a gripper assembly 37 that can grasp the vials and is operated by a control system having a processor and memory.

Referring to FIG. 3, the illustrated storage unit 34 also includes a feeder 39 to help load filled vials into the unit 34. The feeder 39 allows a user to position a group of filled vials on the storage unit 34 without having to manually load the vials into particular locations within the storage space 35. Instead, the filled vials can be placed on the feeder 39 by the user, and the gantry assembly 36 can load the vials from the feeder 39 into the storage space 35. Such an arrangement allows the user to rapidly feed filled vials into the storage unit 34 without having to check and confirm the proper location for each vial within the storage space 35. As the gantry assembly 36 loads the vials into the storage space 35, the control system (which may be integrated with the control system of the devices 28) tracks the location of each of the vials in the storage unit 34. In the illustrated embodiment, the feeder 39 includes a horizontal shelf with a series of cubby holes, or ports, for temporarily receiving the vials. In other embodiments, the feeder 39 may include a vertical dispenser column or other suitable structure that receives the vials until the vials are loaded into the storage space 35 by the gantry assembly 36.

The storage unit 34 also includes an automatic scanner 40 (e.g., a bar code scanner, a RF scanner, etc.) and a scale 41. The scanner 40 identifies the vials as the vials move into and/or out of the unit 34. The scanner 40 thereby helps track the location of each vial within the storage space 35 as the gantry assembly 36 moves the vials. The scale 41 weighs the vials as the vials are loaded into the storage unit 34 to verify that the vial was properly filled. For example, the scanner 40 scans the vial to determine the type and amount of pharmaceuticals that are expected to be in the vial, and the scale 41 weighs the vial to determine the weight of the vial. The control system then compares the weight of the vial to an expected weight (based on information stored in a database) to determine whether the vial was properly filled. If properly filled, the vial is loaded into and stored in the storage unit, and the location of the vial is saved in memory. If improperly filled, a notification (e.g., a text message, email alert, alarm, audible message, displayed message, etc.) is delivered to the user. The user can then refill the vial properly and load the refilled vial onto the feeder 40. In some embodiments, the scanner 40 and the scale 41 can be integrated into the gripper assembly 37 of the gantry assembly 36 such that the scanning and weighing functions occur as the gantry assembly 26 moves and loads the vials. In other embodiments, such as the illustrated embodiment, the scanner 40 and the scale 41 may be located on the feeder 40.

The illustrated will call area 18 also includes a secondary storage machine 38 for receiving and storing containers that have different sizes and shapes than the vials. In particular, the containers are shaped and sized such that they are incompatible with (i.e., too large, bulky, or cumbersome for) the storage unit 34. The containers are filled "unit of use" packs such as, for example, inhalers, syringes, bandages, patches, and other devices not suitable for storage in a prescription vial. The secondary storage machine 38 may include a rotating rubber belt with vanes to divide and move the filled packs to an exit port. An inlet port 43 in a top surface of the storage machine 38 allows a user to insert containers into the machine 38 between the vanes. In some embodiments, removable patient labels may be applied to the filled packs before the patient-specific packs are placed in the secondary storage machine 38 to help identify the packs. Additionally or alternatively, the storage machine 38 may be refrigerated for storing certain types pharmaceuticals, such as insulin.

When a customer arrives to pick up his or her prescription, the filled prescription vials can be dispensed from the storage unit 34 through tubes 42 or other suitable conduits. The tubes 42 extend from an outlet of the storage unit 34 generally toward the sales area 22. The tubes 42 are configured to receive one or more vials from the gantry assembly 36 to direct the vials toward the customer. In other embodiments, the containers may be moved out of the machine by gravity when, for example, the container passes over and drops through a hole. In the illustrated embodiment, each tube 42 includes a sensor 44 (e.g., an infrared or laser beam) that detects movement of the vials through the tube 42. The sensors 44 verify that a vial actually was dispensed out of the storage unit 34.

Similarly, the filled containers may be dispensed from the secondary storage machine 38 through tubes 46 or other suitable conduits. The tubes 46 extend from the exit port of the machine 38 generally toward the sales area 22. As the belt within the machine 38 rotates, a plunger or other suitable mechanism within the machine 38 pushes the containers through the exit port and into the tubes 46. In the illustrated embodiment, each tube 46 includes a sensor 48 (e.g., an infrared or laser beam) that detects movement of the containers through the tube 46. The sensors 48 verify that a container actually was dispensed out of the secondary storage machine 38.

The sales area 22 receives the filled vials and containers from the will call area 18. The illustrated sales area 22 includes two automated or self-serve kiosks 50 and a counter 54. Depending on where a customer goes to pick up his or her prescription, the storage unit 34 and the secondary storage machine 38 may dispense the filled prescription to either one of the kiosks 50 or a pharmacist working at the counter 54.

The self-serve kiosks 50 include touch screens, signature capture systems, and credit/debit payment systems. In some embodiments, the kiosks 50 may require a customer to login using a username and/or password in order to use and operate the kiosks 50. The kiosks 50 also include a slidable bank drawer-type device and a printer. The drawer-type device receives the filled prescription from the tubes 42, 46 and releases the prescription to a customer once identification and payment are approved. The printer prints associated paperwork for the prescription, such as instructions for use and receipts. In some embodiments, the printer may not print the paperwork until requested by the customer. Such an arrangement reduces paper waste if the customer is already familiar with the prescription. Each kiosk 50 can also include a camera to monitor the customer as the customer interacts with the kiosk 50. Unlike the counter 54, the kiosks 50 allow a customer to pick up his or her prescription after hours when a pharmacist is no longer available.

Each kiosk 50 may also include a detector or sensor to detect that the customer actually takes the prescription and printed material from the kiosk 50. The kiosks 50 may also include a recovery feature to "pull back" filled vials and packs (as well as any associated printed material) if a customer walks away without taking his or her prescription. For example, if the customer does not open the lid of the drawer-type device within a certain period of time (e.g., one minute), the drawer of the kiosk 50 can automatically slide back behind a wall of the pharmacy and drop the unclaimed prescription into a collection bin. This feature can help protect confidential patient healthcare information.

The filled vials and packs from the will call area 18 can alternatively be dropped into catch bins 58 behind a wall of the pharmacy. The bins 58 are accessible directly by the pharmacy staff. The bins 58 allow the vials and packs to be delivered to customers from a pharmacist, or other staff member, working at the counter 54 rather than through the kiosks 50. In some embodiments, the bins 58 may be locked such that each bin 58 is accessible only to a particular user (e.g., a pharmacist, technician, clerk, etc.). The bins 58 may be coded or keyed to require a user to login to access each of the bins 58. Such an arrangement inhibits different users from opening the wrong bins 58 and accessing the wrong prescriptions.

The storage unit 34 and the secondary storage machine 38 allow storage of filled vials and packs without printing drug information and/or patient-specific information on, for example, a monograph. Such an arrangement reduces the amount of storage space needed for the monographs. Instead, the monograph can be printed when the customer arrives to pick up the vial or pack at one of the kiosks 50 or at the counter 54. A customer can also choose not to have this information printed if the customer is already familiar with the prescription, reducing excess paper waste. In addition, by not printing monographs or packing the filled vials and packs before a customer claims his or her prescription, the pharmacy does not need to shred and dispose of unused monographs or provide extra storage space for unused bags. Furthermore, by placing the filled vials and packs in a sales pending state within the storage unit 34, a multi-part prescription order does not need to be disassembled if all or part of the order is unclaimed or canceled by a customer.

The storage unit 34 and the secondary storage machine 38 can also automatically return filled vials and containers to the pharmaceutical storage and retrieval devices 28 if the vials or containers are canceled by a customer or unclaimed by the customer after a predetermined period of time. Once a prescription order is filled, the filled vials or containers are loaded into the storage unit 34 or the storage machine 38, as described above. The control system monitors a length of time that the vials and containers are stored in the unit 34 or the machine 38. Alternatively, the control system can monitor a length of time from when the prescriptions are filled. If the filled vials and containers are unclaimed after, for example, ten days, the storage unit 34 and the secondary storage machine 38 direct the unclaimed vials and containers to a tote or bin (e.g., one of the bins 58) behind a wall of the pharmacy for restocking in the devices 28. The gantry assembly 36 in the storage unit 34 and the plunger in the secondary storage machine 38 are operated by the control system to direct the unclaimed vials and containers into a suitable bin using one of the corresponding conduits 42, 46. This automatic unloading may occur overnight while the pharmacy is closed and not in operation.

In the morning, pharmacy staff collects the unclaimed vials and containers from the bin. The staff then transfers the vials and containers back to the pharmaceutical storage and retrieval devices 28 in the production area 14 by inserting the filled vials and containers into inlet ports in the devices 28. The unclaimed, filled vials and containers are thereby placed back into stock. The filled vials and containers are returned to the devices 28 without removing the pharmaceuticals stored inside the vials and containers. In some scenarios, patient labels may also be left on the vials because the devices 28 are enclosed and, thereby, prevent users or other personnel from reading or accessing the pharmaceuticals (and the associated personal healthcare information) stored in the devices 28. That is, the labels do not need to be altered (e.g., blacked-out, removed, or otherwise obliterated) when the vials are returned to the devices 28. In such scenarios, the vials may be re-dispensed if the appropriate customer ever arrives to claim the vials. Alternatively, the patient labels may be removed once the vials are needed to fill a prescription order for a different customer.

The system 10 requires fewer technicians to fill orders, maintains accurate inventory in a secure manner, allows visibility of finished (e.g., filled) vial and pack inventory, and stores the finished inventory securely. The system 10 thereby provides, among other things, higher security, accuracy in delivering the correct items to patients, a single location for storage of all finished/filled goods, and a kiosk delivery system for self-checkout.

Figure 4:
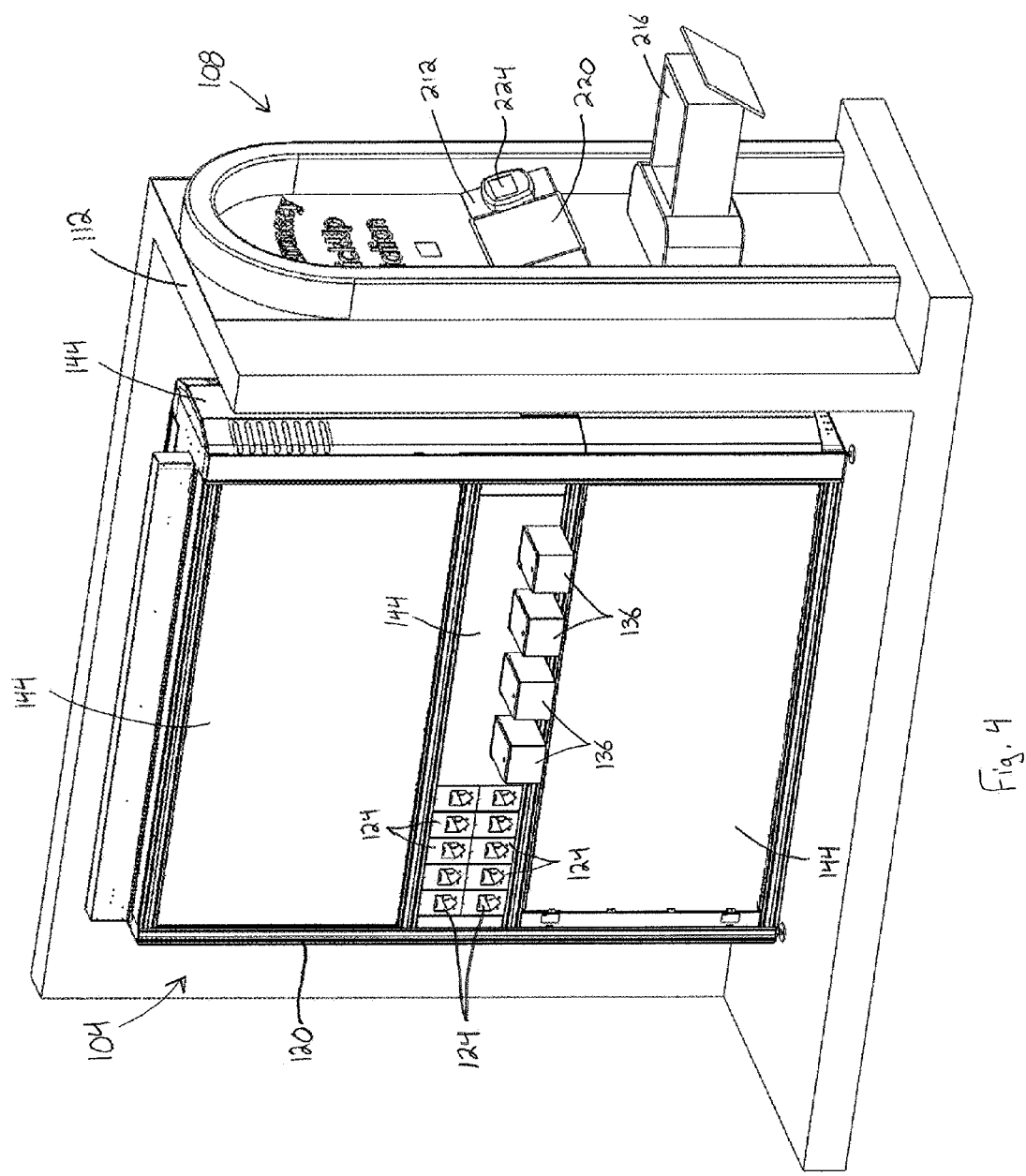
FIG. 4 is a perspective view of a storage unit and a kiosk for use in the pharmacy.
Figure 5:
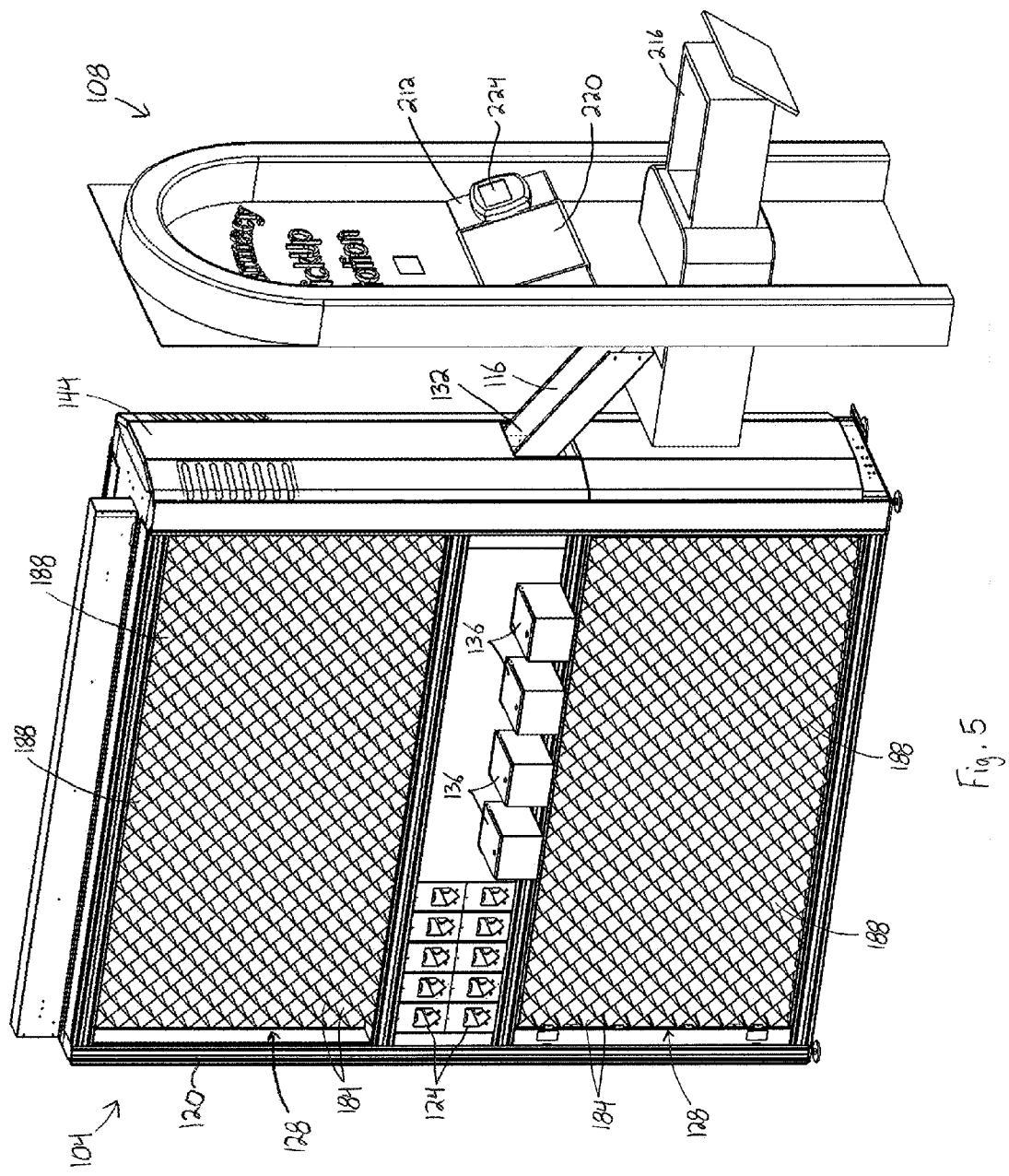
FIG. 5 is another perspective view of the storage unit and the kiosk with panels removed from the storage unit.

FIGS. 4 and 5 illustrate an example of a storage unit 104 and a self-serve kiosk 108 for use with the system 10. As shown in FIG. 4, the storage unit 104 and the kiosk 108 are separated by a wall 112. The storage unit 104 and the kiosk 108 are positioned on opposite sides of the wall 112 within the pharmacy such that a customer accessing the kiosk 108 cannot access the storage unit 104 directly. Instead, as shown in FIG. 5, the storage unit 104 communicates with the kiosk 108 via a chute 116 to direct filled prescription orders toward the kiosk 108 when the prescription orders are claimed by the customer. As noted above, the filled prescription orders may be patient-specific orders or stock pharmaceutical orders.

Figure 6:
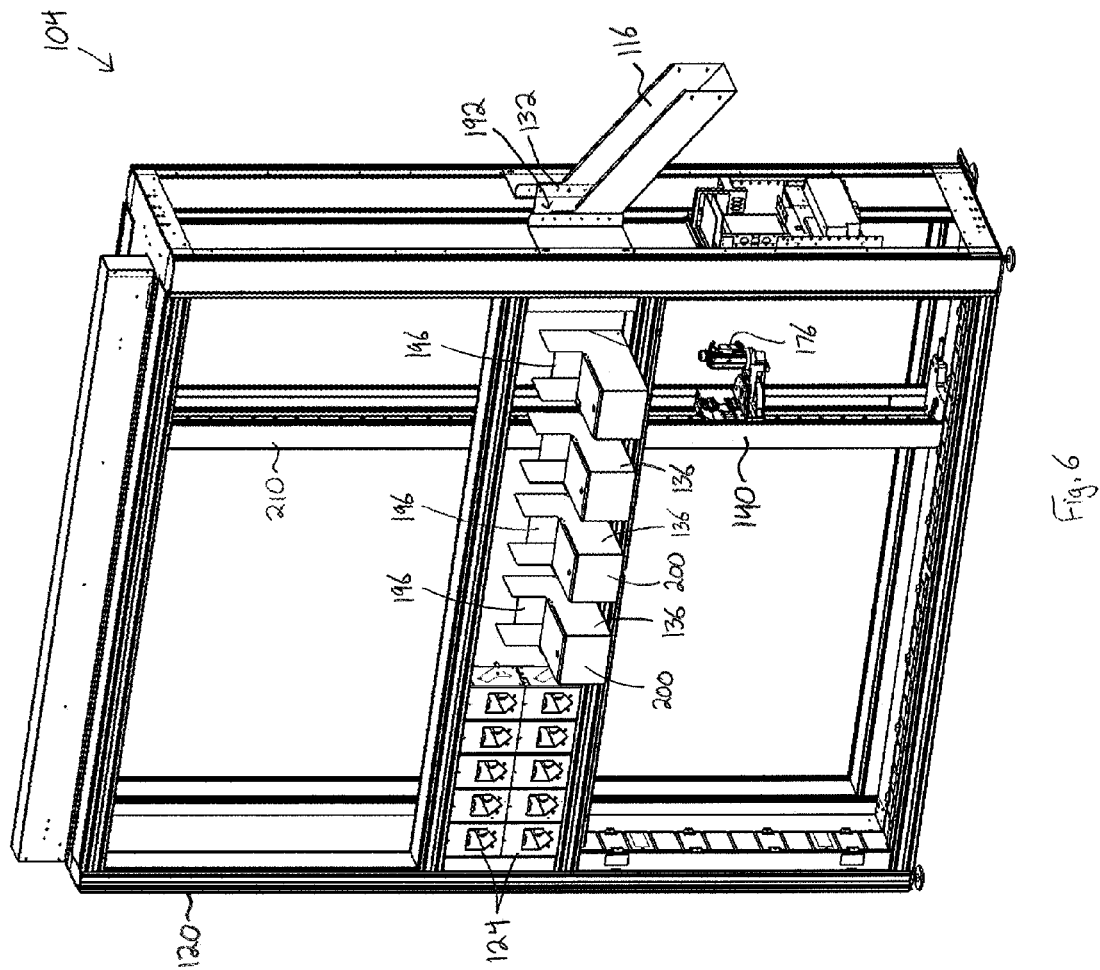
FIG. 6 is a perspective view of the storage unit with a storage structure removed from the storage unit.

As shown in FIGS. 5 and 6, the illustrated storage unit 104, or tower, includes a frame 120, a plurality of feeders 124 mounted to the frame 120, a storage structure 128 positioned within the frame 120, a dispenser 132 mounted to the frame 120, a plurality of collection bins 136 mounted to the frame 120, and a container-moving assembly 140 positioned within the frame 120. The frame 120 supports the other components of the storage unit 104 and defines an outer periphery of the unit 104. As shown in FIG. 4, the frame 120 also includes outer panels 144 that enclose the storage unit 104. The panels 144 inhibit a user from accessing the inside of the storage unit 104 and, more particularly, the filled prescription orders stored within the unit 104.

The feeders 124 are mounted to the frame 120 such that the feeders 124 are accessible to a user (e.g., a pharmacist, a technician, a clerk, etc.) from outside of the storage unit 104. The feeders 124 allow the user to insert or load filled prescription orders (e.g., from the production area system 26 shown in FIGS. 1-3) into the storage unit 104. In the illustrated embodiment, the storage unit 104 includes eight feeders 124 arranged in two, stacked rows on a side of the frame 120. Providing eight feeders 124 allows a user to load eight filled prescription orders into the storage unit 104 simultaneously without having to wait for the container-moving assembly 140 (FIG. 6) to move the orders out of the feeders 124. In other embodiments, the storage unit 104 may include fewer or more feeders 124 located elsewhere on the frame 120.

Figure 7:
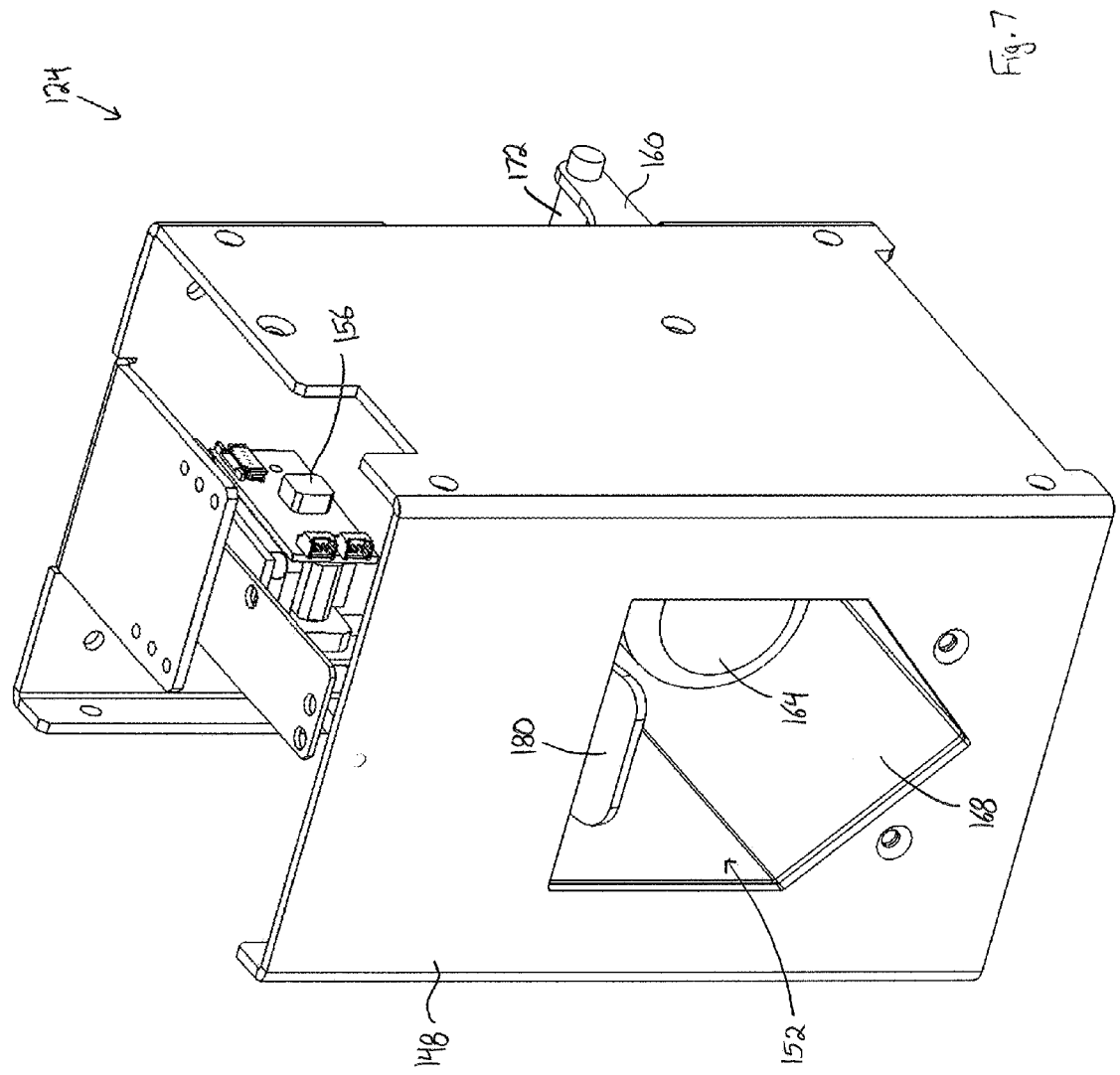
FIG. 7 is a front perspective view of a feeder of the storage unit.
Figure 8:
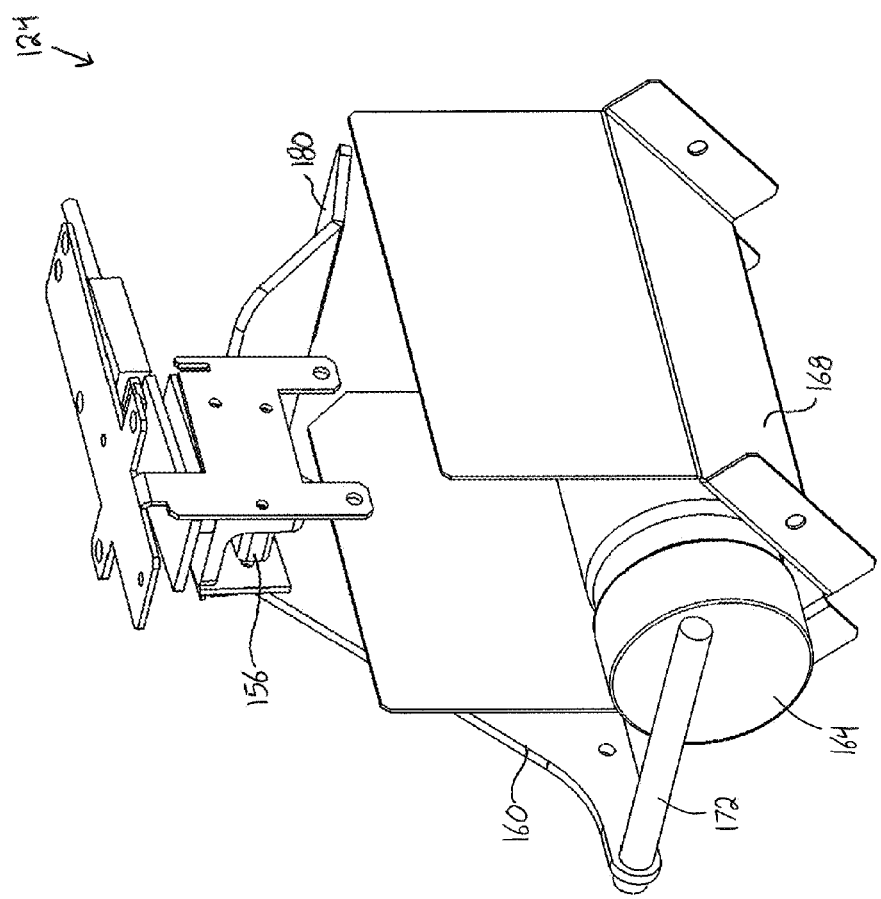
FIG. 8 is a rear perspective view of the feeder of the storage unit, the feeder including a positioning member in a first position.
Figure 9:
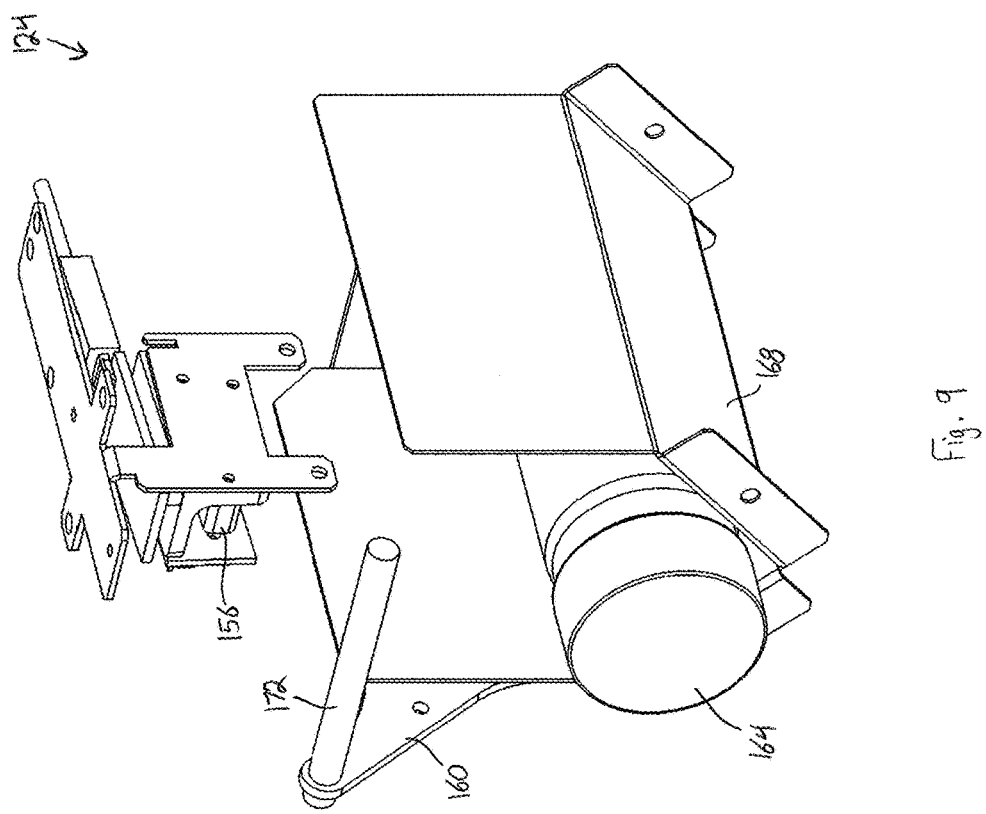
FIG. 9 is another rear perspective view of the feeder of the storage unit with the positioning member in a second position.

As shown in FIGS. 7-9, each feeder 124 includes a housing 148, a loading port 152, a scanner 156, and a positioning member 160. The housing 148 defines the loading port 152 and supports the scanner 156 and the positioning member 160. The housing 148 is also configured to be secured (e.g., bolted) to the frame 120 and the other adjacent feeders 124 to mount the feeder 124 to the frame 120. The housing 148 is generally compact and cube-shaped such that the feeder 124 is a self-contained unit that can be assembled on the frame 120 in a modular fashion.

The loading, or inlet, port 152 extends through the housing 148 and is configured to receive a filled prescription order (e.g., a filled vial 164). The loading port 152 temporarily stores the filled vial 164 until the vial 164 is grabbed by the container-moving assembly 140 and moved to the storage structure 128. In the illustrated embodiment, a bottom of the loading port 152 is defined by a generally V-shaped wall 168 of the housing 148. The V-shaped wall 168 inhibits the filled vial 164 from rolling within the loading port 152 when the vial 164 is inserted into the port 152 and rests on the wall 168.

The scanner 156 is positioned generally above the loading port 152 to read a label on the filled vial 164. The illustrated scanner 156 may be, for example, a barcode or quick response (QR) code scanner. The scanner 156 is in communication with a control system of the storage unit 104 to help track a location of the vial 164. When the filled vial 164 is positioned within the loading port 152, the scanner 156 reads the label to identify the particular vial 164. The control system identifies into which feeder 124 the filled vial 164 was loaded and can track where the container-moving assembly 140 moves the vial 164 within the storage unit 104.

Figure 10:
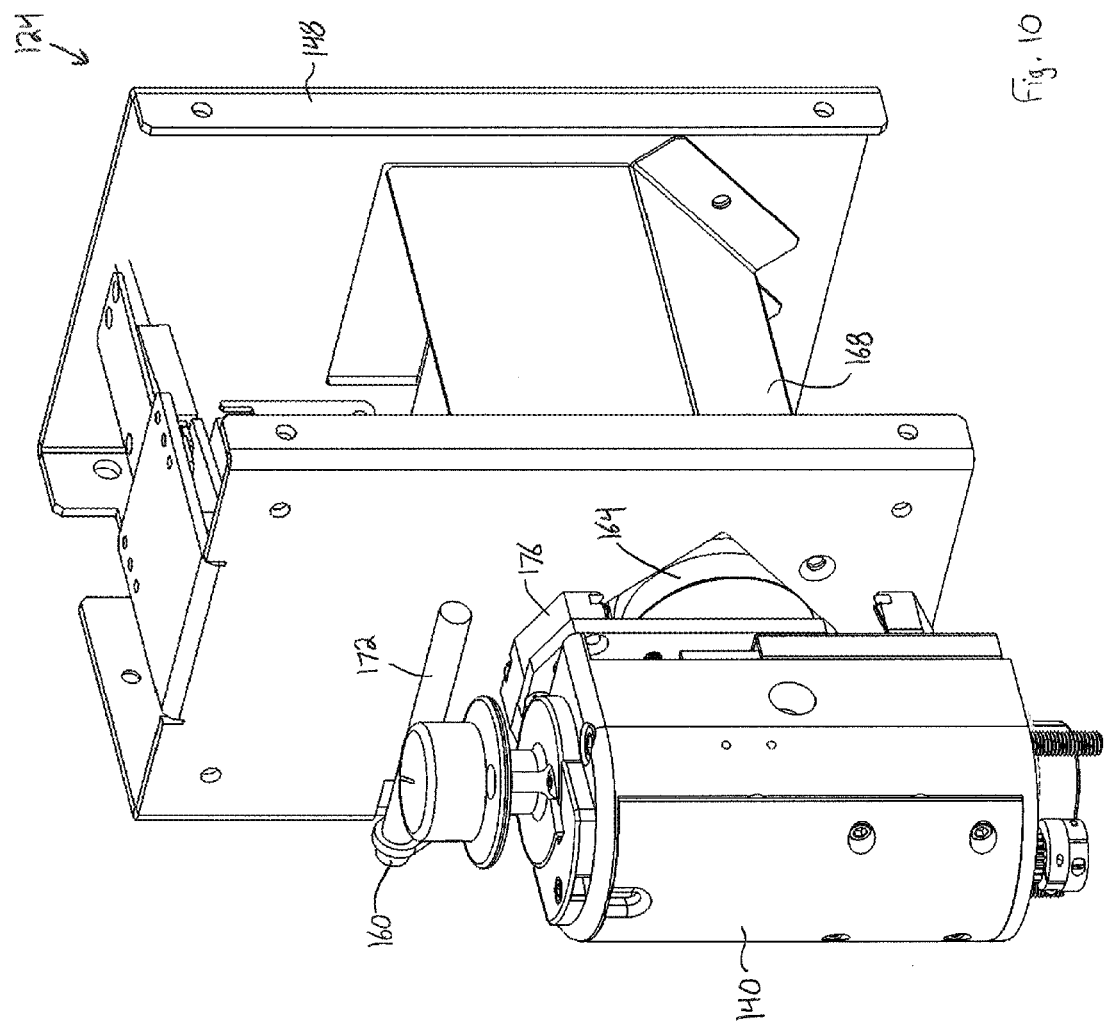
FIG. 10 is a rear perspective view of the feeder of the storage unit with a gantry assembly engaging a vial in the feeder.

The positioning member 160 is coupled to the housing 148 adjacent the loading port 152. The positioning member 160 facilitates properly positioning the filled vial 164 within the port 152 such that the vial 164 is accessible by the container-moving assembly 140. As shown in FIG. 8, the positioning member 160 includes a bar 172 that extends across an inner side of the loading port 152 (i.e., the side of the loading port 152 that is accessible from within the frame 120). The bar 172 provides a physical stop for the filled vial 164. Pushing the vial 164 against the bar 172 helps ensure that the filled vial 164 is inserted into the loading port 152 far enough so that the vial 164 can be engaged and grasped by a gripper head 176 of the container-moving assembly 140, as shown in FIG. 10.

The positioning member 160 is also movable (e.g., pivotable) relative to the housing 148 to move the bar 172 out of the way of the gripper head 176 of the container-moving assembly 140. The positioning member 160 is movable between a first position (FIGS. 7-8), in which the bar 172 engages the filled vial 164, and a second position (FIGS. 9-11), in which the bar 172 is moved out of engagement with the filled vial 164 to allow access to the vial 164 by the container-moving assembly 140. As shown in FIGS. 9 and 10, the positioning member 160 can be pivoted to lift the bar 172 away from the filled vial 164. In some embodiments, the bar 172 may be lifted automatically by a solenoid or by the gripper head 176 as the container-moving assembly 140 approaches the feeder 124. In other embodiments, the bar 172 may be manually pivoted out of the way of the gripper head 176. For example, as shown in FIGS. 7 and 11, the positioning member 160 includes a manual actuator 180 extending from an outer side of the loading port 152 (i.e., the side of the loading port 152 that is accessible from outside of the frame 120). The illustrated manual actuator 180 is a tab. The actuator 180 allows a user to manually pivot the positioning member 160 relative to the housing 148 to lift the bar 172. In addition, when actuated (FIG. 11), the actuator 180 substantially blocks the outer side of the loading port 182 to inhibit a user from pulling the filled vial 164 away from the gripper head 176 or otherwise accessing the container-moving assembly 140.

In some embodiments, each feeder 124 may also include a scale. In such embodiments, the feeders 124 may weigh the filled vials 164 when the vials 164 are inserted into the loading ports 152. The scale may be, for example, incorporated into the V-shaped wall 168 of the housing 148 such that the filled vials 164 are weighed when they are resting on the wall 168. The scale may work in conjunction with the scanner 156 to determine whether the correct type and amount of pharmaceuticals are present within each vial 164 by comparing the actual weight of the vial 164 to an expected weight of the vial 164.

Referring back to FIG. 5, the storage structure 128 is positioned within and supported by the frame 120. The storage structure 128 is configured to store the vials 164 that are loaded into the unit 104 through the feeders 124. The storage structure 128 is covered by the outer panels 144 (FIG. 4) of the frame 120 such that the structure 128 and the stored vials 164 are not accessible or visible to a user from outside of the unit 104.

In the illustrated embodiment, the storage structure 128 includes a plurality of support members 184 that intersect each other to form a honeycomb-type pattern. The honeycomb-type pattern defines a plurality of diamond-shaped storage spaces 188 between the support members 184. Each storage space 188 is configured to receive one of the filled vials 164 at a time so that each vial 164 is stored within the storage structure 188 at a discrete location. The honeycomb-type pattern formed by the support members 184 increases the storage density of the unit 104 compared to a storage structure having horizontal shelves. The honeycomb-type pattern also inhibits the vials 164 from moving (e.g., rolling, shifting, etc.) within the storage spaces 188. Although not shown, a second, similarly-configured support structure is positioned on the other side of the frame 120 and the container-moving assembly 140 to store additional vials within the storage unit 104.

The dispenser 132 is mounted to the frame 120 to dispense the filled vials 164 out of the storage unit 104. The illustrated dispenser 132 includes a discharge port 192 formed in the frame 120 and the chute 116 extending from the discharge port 192. The discharge port 192 receives the vials 164 from the container-moving assembly 140 when requested by, for example, a customer. The chute 116 directs the requested vials 164 from the discharge port 192 toward the customer. More particularly, the chute 116 extends between the discharge port 192 and the kiosk 108 to direct the requested vials 164 into the kiosk 108. In other embodiments, other suitable conveyors, ramps, or funnels may be employed to direct the requested vials 164 from the discharge port 192 into the kiosk 108. In some embodiments, the dispenser 132 may include a sensor (e.g., a scanner, a laser beam, a camera, etc.) at the discharge port 192 to verify that the requested vial 164 was properly dispensed from the storage unit 104.

The collection bins 136 are mounted to the frame 120 adjacent the feeders 124. The collection bins 136 are secure boxes that receive the vials 164 from within the storage unit 104 for access by a user (e.g., a pharmacist, a technician, a clerk, etc.) behind the wall 112 (FIG. 4) of the pharmacy, rather than by a customer using the kiosk 108. The collection bins 136 allow the user to retrieve a particular vial from the storage unit 104 if a customer prefers to purchase his or her prescription over a counter directly from a person, instead of by using the kiosk 108. Alternatively, the collection bins 136 allow the user to return canceled or unclaimed orders to the production area 14 (FIGS. 1-3). In the illustrated embodiment, the storage unit 104 includes four collection bins 136 arranged in a row on the side of the frame 120. In other embodiments, the storage unit 104 may include fewer or more collection bins 136 and/or the collection bins 136 may be located elsewhere on the unit 104.

As shown in FIGS. 12 and 13, each of the illustrated collection bins 136 includes a first portion 196 positioned within the frame 120 and a second portion 200 extending out of the frame 120. The first portion 196 is accessible to the container-moving assembly 140 from within the frame 120. The second portion 200 is accessible to a user from outside of the frame 120. The first and second portions 196, 200 are separated from each other by one of the outer panels 144 (FIG. 4) of the frame 120. The first portion 196 is generally open to provide access for the container-moving assembly 140 to move (e.g., drop) a vial 164 into the collection bin 136. The second portion 200 is generally enclosed to limit access to the vial(s) 164 within each collection bin 136 from outside of the frame 120.

In the illustrated embodiment, the second portion 200 includes a lid 204 and a lock 208 to limit access into the collection bin 136. The lid 204 is movable (e.g., pivotable) between an open position (FIG. 13) and a closed position (FIG. 12). The lock 208 selectively secures the lid 204 in the closed position such that only authorized users may open the lid 204. In some embodiments, the lock 208 may be opened by a physical key. In such embodiments, only users who have access to the key for a particular lock 208 may open the lid 204 to retrieve the vial(s) 164 from inside the collection bin 136. In other embodiments, the lock 208 may be opened by a password, passcode, or biometric verification from the user. The locks 208 limit the number of people within the pharmacy who can access the filled vials 164 stored within the storage unit 104. In addition, the locked collection bins 136 reduce the possibility of a user accessing the incorrect collection bin 136 and grabbing the wrong vial(s) 164. For example, each of the collection bins 136 may be assigned to one particular user so that only that user can access the collection bin 136 during his or her shift.

As shown in FIG. 6, the container-moving assembly 140, or gantry assembly, includes a rail 210 and the gripper head 176 to move the filled vials 164 within the storage unit 104. The rail 210 is movable horizontally relative to the frame 120, while the gripper head 176 is movable vertically along the rail 210. The illustrated rail 210 extends vertically between an upper portion and a lower portion of the frame 120 to ride along tracks formed in the frame 120. The gripper head 176 is mounted to the rail 210 to ride along a track formed in the rail 210. In the illustrated embodiment, the rail 210 and the gripper head 176 are driven by electric motors positioned within the frame 120. Together, the rail 210 and the gripper head 176 operate similar to the gantry assembly discussed in U.S. patent application Ser. No. 12/870,045 to move throughout the interior of the storage unit 104.

The container-moving assembly 140 is coupled to and controlled by the control system of the storage unit 104. The container-moving assembly 140 is operable to move the vials 164 from each of the feeders 124 to the storage structure 128. The container-moving assembly 140 is also operable to move the vials 164 from the storage structure 128 to the dispenser 132 or to the collection bins 136. The container-moving assembly 140 moves the vials 164 to the dispenser 132 when the assembly 140 receives a first command, or signal, from the control system of the storage unit 104. The first command coincides with, for example, a customer claiming his or her prescription order at the kiosk 108.

Alternatively, the container-moving assembly 140 moves the vials 164 to one of the collection bins 136 when the assembly 140 receives a second command, or signal, from the control system of the storage unit 104. The second command coincides with, for example, a user (e.g., a pharmacist, a technician, a clerk, etc.) requesting the vial 164 to sell the vial 164 directly to the customer, the prescription order being canceled by the customer, or the prescription order being unclaimed by a customer after a predetermined period of time. In some embodiments, the storage unit 104 may hold a filled prescription for up to ten days before the order is considered to be unclaimed and, therefore, moved to one of the collection bins 136. The amount of time required to pass before an order is considered unclaimed may be set and varied by the operator of the pharmacy.

Referring to FIGS. 5 and 6, the illustrated kiosk 108 includes a user interface 212 and a drawer 216. The user interface 212 is coupled to the control system of the storage unit 104 to communicate with the storage unit 104. The user interface 212 includes, for example, a touch screen 220 and a credit card swipe 224. The user interface 212 allows a user to interact with the kiosk 108, and thereby the storage unit 104, to claim his or her prescription order(s) from the storage unit 104. For example, the user can login to the kiosk 180 using a password or a credit/debit card, review information regarding available prescription orders, and pay for the desired prescription orders using the credit card swipe 224. The user interface 212 also allows a user to decide whether to print monographs, receipts, or other paperwork associated with the prescription orders at the kiosk 108.

Once the user is verified and the desired prescription orders are paid for, the storage unit 104 dispenses the corresponding vials 164 into the drawer 216. The drawer 216 may slide relative to the kiosk 108 and the wall 112 like a bank drawer to securely dispense the vials 164 to the customer. Furthermore, the drawer 216 may automatically pull back into the kiosk 108 and the wall 212 after a short period of time in case the customer accidently leaves one or more vials unclaimed within the drawer 216. Once behind the wall 212, the unclaimed vials may drop through a hole in the bottom of the drawer 216 and into a basket or tote.

In some embodiments, a single storage unit 104 may communicate with more than one kiosk 108. In other embodiments, multiple storage units 104 may communicate with a single kiosk 108 or with multiple kiosks 108.

The storage unit 104 and the kiosk 108 are configured to allow a user to claim all or part of his or her prescription order using the kiosk 108. Since the storage unit 104 stores each of the filled vials 164 individually, if a user decides to only pickup part of the order, only the requested vials 164 are moved by the container-moving assembly 140 to the dispenser 132. The remaining, unclaimed vials 164 can be left inside of the storage unit 104 until the vials 164 are picked up at a later date or ultimately canceled. As such, when a user only claims part of the order, the entire order does not need to be disassembled and repackaged to sell the claimed portion of the order to the customer.

If a particular order (or part of an order) remains unclaimed after a predetermined period of time (e.g., ten days), the order may be automatically moved by the container-moving assembly 140 to one of the collection bins 136. Alternatively, if a customer decides at the kiosk 108 to explicitly cancel all or part of the order, the container-moving assembly 140 can immediately (or at its next free/unused time) move the canceled order from the storage structure 128 to one of the collection bins 136. After a vial 164 is moved into one of the collection bins 136, the control system of the storage unit 104 can notify a user (e.g., via email, text message, or other audio or visual alert) that the order was unclaimed or canceled and in which collection bin 136 the order is located. If authorized, the user can then retrieve the unclaimed or canceled order from the collection bin 136 to return the order to the production area system 26 (FIGS. 1-3).

Various features and advantages of the invention are set forth in the following claims.

The invention claimed is:

1. A storage unit for storing and dispensing filled prescription orders, the storage unit comprising:
   a frame;
   a feeder mounted to the frame, the feeder including a loading port configured to receive a container containing a filled prescription order;
   a storage structure positioned within the frame, the storage structure configured to store containers containing the filled prescription orders;
   a dispenser mounted to the frame, the dispenser configured to dispense the containers containing the filled prescription orders;
   a collection bin mounted to the frame, the collection bin configured to receive the containers containing the filled prescription orders;
   a container-moving assembly positioned within the frame, the container-moving assembly operable to move the container containing the filled prescription order from the feeder to the storage structure when the container is positioned within the feeder, move the container from the storage structure to the dispenser in response to a first command, and move the container from the storage structure to the collection bin in response to a second command; and a plurality of feeders mounted to the frame, the plurality of feeders including a plurality of loading ports to allow loading a plurality of containers containing filled prescription orders into the storage unit simultaneously, each feeder including a V-shaped wall that forms a bottom of the corresponding loading port.

2. The storage unit of claim 1, wherein the container-moving assembly moves the filled prescription order from the storage structure to the dispenser when the filled prescription order is claimed by a customer.

3. The storage unit of claim 1, wherein the container-moving assembly moves the filled prescription order from the storage structure to the collection bin when the filled prescription order is one of requested by a user, canceled by a customer, and unclaimed after a predetermined period of time.

4. The storage unit of claim 1, further comprising a plurality of collection bins mounted to the frame, wherein each collection bin is configured to receive the filled prescription orders, and wherein the container-moving assembly is operable to move the filled prescription orders from the storage structure to each of the collection bins in response to the second command.

5. The storage unit of claim 1, wherein the feeder includes a loading port and a scanner, wherein the loading port is configured to receive a filled prescription order, and wherein the scanner is operable to read a label on the filled prescription order when the filled prescription order is positioned within the loading port.

6. The storage unit of claim 1, wherein the feeder includes a loading port and a positioning member, wherein the loading port is configured to receive a filled prescription order, and wherein the positioning member is configured to engage the filled prescription order to properly position the filled prescription order within the loading port for engagement by the container-moving assembly.

7. A storage unit for storing and dispensing filled prescription orders, the storage unit comprising:

a frame;

a feeder mounted to the frame, the feeder configured to receive the filled prescription orders;

a storage structure positioned within the frame, the storage structure configured to store the filled prescription orders;

a dispenser mounted to the frame, the dispenser configured to dispense the filled prescription orders; and a collection bin mounted to the frame, the collection bin configured to receive the filled prescription orders; and a container-moving assembly positioned within the frame, the container-moving assembly operable to move a filled prescription order from the feeder to the storage structure when the filled prescription order is positioned within the feeder, move the filled prescription order from the storage structure to the dispenser in response to a first command, and move the filled prescription order from the storage structure to the collection bin in response to a second command, wherein the collection bin includes a first portion positioned within the frame and a second portion extending out from the frame, wherein the first portion is accessible from within the frame, and wherein the second portion is accessible from outside of the frame, wherein the first portion of the collection bin is open to provide access for the container-moving assembly to move the filled prescription order into the collection bin, and wherein the second portion of the collection bin is enclosed to limit access to the filled prescription order from outside of the frame.

8. The storage unit of claim 7, wherein the second portion of the collection bin includes a lid and a lock, wherein the lid is movable between an open position and a closed position, and wherein the lock selectively secures the lid in the closed position.

9. The storage unit of claim 7, wherein the frame includes an outer panel, and wherein the outer panel separates the first portion of the collection bin from the second portion of the collection bin.

10. The storage unit of claim 7, wherein the container-moving assembly moves the filled prescription order from the storage structure to the dispenser when the filled prescription order is claimed by a customer.

11. The storage unit of claim 7, wherein the container-moving assembly moves the filled prescription order from the storage structure to the collection bin when the filled prescription order is one of requested by a user, canceled by a customer, and unclaimed after a predetermined period of time.

12. A storage unit for storing and dispensing filled prescription orders, the storage unit comprising:

a frame;

a feeder mounted to the frame, the feeder configured to receive the filled prescription orders;

a storage structure positioned within the frame, the storage structure configured to store the filled prescription orders;

a dispenser mounted to the frame, the dispenser configured to dispense the filled prescription orders;

a collection bin mounted to the frame, the collection bin configured to receive the filled prescription orders; and a container-moving assembly positioned within the frame, the container-moving assembly operable to move a filled prescription order from the feeder to the storage structure when the filled prescription order is positioned within the feeder, move the filled prescription order from the storage structure to the dispenser in response to a first command, and move the filled prescription order from the storage structure to the collection bin in response to a second command, wherein the feeder includes a loading port and a positioning member, wherein the loading port is configured to receive a filled prescription order, and wherein the positioning member includes a physical stop extending across an inner side of the loading port and configured to engage the filled prescription order to properly position the filled prescription order within the loading port for engagement by the container-moving assembly, and wherein the positioning member is movable between a first position, in which the physical stop engages the filled prescription order to limit how far the filled prescription order is inserted into the loading port, and a second position, in which the physical stop is moved out of engagement with the filled prescription order to allow access to the filled prescription order by the container-moving assembly.

13. The storage unit of claim 1, wherein the dispenser includes a discharge port and a chute extending from the discharge port, wherein the container-moving assembly is operable to move the filled prescription order from the storage structure to the discharge port in response to the first command, and wherein the chute directs the filled prescription order out of the discharge port.

14. The storage unit of claim 1, wherein the storage structure includes a plurality of support members that intersect each other to form a honeycomb-type storage structure, wherein the honeycomb-type storage structure defines a plurality of storage spaces, and wherein each storage space is configured to receive one of the filled prescription orders.

15. A method of storing and dispensing filled prescription orders from a storage unit, the storage unit including a frame, a feeder mounted to the frame, a storage structure positioned within the frame, a dispenser mounted to the frame, a collection bin mounted to the frame, and a container-moving assembly positioned within the frame, the method comprising:
inserting a filled prescription order into the feeder;
moving, by the container-moving assembly, the filled prescription order from the feeder to the storage structure; and
moving, by the container-moving assembly, the filled prescription order from the storage structure to one of the dispenser and the collection bin, wherein the container-moving assembly moves the filled prescription order to the dispenser in response to a first command and moves the filled prescription order to the collection bin in response to a second command,
wherein the collection bin includes a first portion that is accessible within the storage unit and second portion that is accessible from outside the storage unit, wherein the second portion of the collection bin includes a lid, and further comprising opening the lid to access the filled prescription order within the collection bin.

16. The method of claim 15, wherein the container-moving assembly moves the filled prescription order to the dispenser when the filled prescription order is claimed by a customer.

17. The method of claim 15, wherein the container-moving assembly moves the filled prescription order to the collection bin when the filled prescription order is one of requested by a user, canceled by a customer, and unclaimed after a predetermined period of time.

18. The method of claim 15, wherein the second portion of the collection bin also includes a lock, and further comprising unlocking the lock to open the lid.

19. The method of claim 15, wherein the first portion of the collection bin is open within the storage unit, and wherein moving the filled prescription order from the storage structure to the collection bin includes dropping the filled prescription order into the first portion of the collection bin.

20. The method of claim 15, wherein the feeder includes a scanner, and further comprising reading a label on the filled prescription order with the scanner while the filled prescription order is positioned within the feeder.

* * * * *